(12) United States Patent
Hirabayashi et al.

(10) Patent No.: US 6,478,738 B1
(45) Date of Patent: *Nov. 12, 2002

(54) METHOD OF MASS-ANALYZING BODY FLUID AND APPARATUS THEREFOR

(75) Inventors: Yukiko Hirabayashi, Kokubunji (JP); Atsumu Hirabayashi, Kodaira (JP); Hideaki Koizumi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 77 days.

This patent is subject to a terminal disclaimer.

(21) Appl. No.: 09/695,019

(22) Filed: Oct. 25, 2000

Related U.S. Application Data (63) Continuation of application No. 09/273,554, filed on Mar. 22, 1999, now Pat. No. 6,190,316.

(30) Foreign Application Priority Data

Mar. 25, 1998 (JP) .......................................... 10-077604

(51) Int. Cl.[7] .................................................. A61B 5/00
(52) U.S. Cl. ...................................... 600/309; 250/281
(58) Field of Search ................................ 600/309, 366; 250/281, 282, 288; 422/68.1

(56) References Cited

U.S. PATENT DOCUMENTS 6,190,316 B1 * 2/2001 Hirabayashi et al. ........ 600/309

* cited by examiner

*Primary Examiner*—Eric F. Winakur
(74) *Attorney, Agent, or Firm*—Antonelli, Terry, Stout & Kraus, LLP (57) ABSTRACT

A living body fluid mass-analyzing method introducing a first solution whose osmotic pressure is close to that of a living body fluid into a microdialysis, extracting the living body fluid from the microdialysis, mixing the living body fluid from the microdialysis and an organic solution, and applying a gas around a capillary through which the mixed living fluid flows thereby spraying and ionizing the living body fluid by the gas. Further, the ionized ions are introduced into three dimensional mass-analyzer through an orifice, accumulating the ions in said three dimensional mass-analyzer and sending out the accumulated ions in order of mass to measure mass numbers of the ions.

6 Claims, 6 Drawing Sheets

METHOD OF MASS-ANALYZING BODY FLUID AND APPARATUS THEREFOR

CROSS REFERENCE TO RELATED APPLICATION

This is a continuation of U.S. application Ser. No. 09/273,554, filed Mar. 22, 1999, now U.S. Pat. No. 6,190,316, the subject matter of which is incorporated by reference herein.

BACKGROUND OF THE INVENTION

1. Field of the Invention

The present invention relates to a method of mass-analyzing a body fluid and an apparatus therefor. More particularly, it relates to a method of mass-analyzing a body fluid and an apparatus therefor which, by mass-analyzing each kind of substances contained in a body fluid of an extremely high or low electrical conductivity, allow component analysis of the body fluid to be performed and can be preferably used for identifying each kind of the substance contained in the body fluid.

2. Description of the Prior Art

As a conventional technique concerning a measuring method for identifying each kind of the substances contained in the body fluid, there is known a method in which the measurement is performed using an electrochemical detection method and employing as the criterion an oxidation-reduction potential characteristic of a substance. Also, as another conventional technique, there is known a component-analyzing method that, with the use of the mass spectrometry, allows a substance to be identified from its mass.

Usually, in the mass spectrometry, an analyte solution such as the body fluid, after being ionized, is introduced into a mass spectrometer so as to detect mass of each kind of the substances contained in the analyte solution. As a conventional technique concerning an ionization method used in the mass analysis of this type, there is known, for example, a technique disclosed in literatures such as U.S. Pat. No. 5,130,538. This conventional technique is referred to as an electrospray ionization method. In this method, 2.5 kV or more of high voltage is applied between a metal capillary into which the solution is introduced and a counter electrode, namely, with the high voltage applied to the solution, the solution is sprayed toward the counter electrode over a space to which the electric field is applied. As a result, an electrospray phenomenon occurs, forming a Taylor corn between the metal capillary and the counter electrode. Then, charged droplets, are sprayed from a tip of the Taylor corn.

When an electrical conductivity of the analyte solution falls in the range of $10^{-13}$ to $10^{-5}$ S cm$^{-1}$ (S=Ω$^{-1}$), the electrospray ionization method according to the above-described conventional technique enables a stable ionization to be performed.

As another conventional technique regarding the ionization method for the analyte solution, there is known, for example, a technique disclosed in literatures such as JP-A-7-306193. The ionization method according to this conventional technique is referred to as a sonic spray ionization method. In this method, gas is caused to flow outside the capillary coaxially therewith and thus the analyte solution is forced to be sprayed from a tip of the capillary, thereby generating the charged droplets. Incidentally, it is recognized that quantities of the positive and negative ions thus generated become maximum when velocity of the gas flow at the tip of the capillary is substantially equal to the sonic velocity.

Moreover, in the mass spectrometry in which, after the analyte solution such as the body fluid has been ionized, the ionized particles are introduced into the mass spectrometer so as to perform the mass analysis, in the case of mass-analyzing a mixture solution in which many kinds of substances are mixed, it is a common practice to employ the following technique: The substances contained in the mixture solution are separated from each other using a member such as a liquid chromatograph or a capillary electrophoresis system, and after that, the mass analysis is performed using the mass spectrometer.

The conventional technique according to the above-described electrochemical detection method is a method in which the measurement is performed employing as the criterion the oxidation-reduction potential characteristic of a substance. As a result, the conventional technique has a problem that an accurate measurement is impossible regarding a living body and, in particular, regarding a substance such as a neurotransmitter the oxidation-reduction potential of which varies with a lapse of time.

Also, in a conventional technique that uses a non-ion trap mass-analyzing apparatus, no matter which method of the electrospray ionization method and the sonic spray ionization method is employed when performing the ionization, in the case of mass-analyzing the body fluid in which many kinds of substances are mixed, the following process is required: The body fluid is separated for each kind of the substances mixed, and after that, the ionization is carried out and then the mass analysis is carried out using the mass spectrometer. The conventional technique, accordingly, necessitates a considerable time for this separation and, as a result, has a problem that mass analysis cannot be performed accurately toward the analyte solution such as the body fluid in which the substances contained vary with a lapse of time and thus values of the corresponding masses also vary with a lapse of time.

Also, in the conventional technique that uses the electrospray ionization method in association with the mass-analyzing apparatus, as explained already, it is difficult to perform the stable ionization if the electrical conductivity of the analyte solution falls outside the range of $10^{-13}$ to $10^{-5}$ S cm$^{-1}$ (S=Ω$^{-1}$). As a result, the conventional technique has a problem that, toward the analyte solution such as the body fluid having an extremely high electrical conductivity, the mass analysis could not be performed.

SUMMARY OF THE INVENTION

It is an object of the present invention to solve the above-described problems in the conventional techniques and thus to provide a configuration embodying a method of mass-analyzing a body fluid and an apparatus therefor which, even toward the analyte solution in which the substances contained vary with a lapse of time and the analyte solution such as the body fluid having an extremely high electrical conductivity, allow the ionization thereof to be performed in a short while, thus making it possible to mass-analyze the analyte solution in a short while.

A new recognition has been obtained that an ionization source using the sonic spray ionization method makes it possible to ionize the analyte solution regardless of how high or low the electrical conductivity of the analyte solution is. In the present invention, the above-described problems have been solved by paying an attention to a combination of this recognition and an ion trap mass spectrometer that allows the mass analysis to be performed in a short while.

Namely, according to the present invention, in a method of mass-analyzing a body fluid, which performs component analysis of the body fluid, an ionization source according to the sonic spray ionization method is employed as an ionization source, and an ion trap three dimensional quadrupole mass spectrometer is employed as a mass spectrometer, and after an analyte solution containing a mixture of living body substances is ionized directly by the above-mentioned ionization source without being separated for each of the substances, the ions are introduced into the mass spectrometer, thereby accomplishing the above-described object.

Also, the above-described living body substances are collected as the analyte solution from a living body with a microdialysis probe, and the mass analysis is performed in real time by immediately introducing the analyte solution into the ionization source from the microdialysis probe through a flowing passage, and also a volatile organic solvent is added to the above-described analyte solution in order to promote the ionization even further, thereby accomplishing the above-described object.

Moreover, in an apparatus for mass-analyzing a body fluid, which performs component analysis of the body fluid, an ionization source using the sonic spray ionization method and an ion trap three dimensional quadrupole mass spectrometer are provided, and after an analyte solution containing a mixture of living body substances is ionized by the above-mentioned ionization source without being separated for each of the substances, the ions are introduced into the mass spectrometer, thereby accomplishing the above-described object.

Also, a microdialysis probe for collecting a body fluid from a living body is provided, and the mass analysis is performed in real time by immediately introducing an analyte solution containing the collected body fluid into the ionization source from the microdialysis probe through a flowing passage, thereby accomplishing the above-described object. Furthermore, a configuration for promoting the ionization of the analyte solution is provided by applying a voltage between an electrode, which is provided in the proximity of a capillary constituting the above-mentioned ionization source, and the analyte solution so that an electric field is applied to the analyte solution, and also a member for eliminating contaminants contained in the solution to be analyzed is provided at the front of an ion-introducing orifice of the above-mentioned mass spectrometer, thereby accomplishing the above-described object.

DETAILED DESCRIPTION OF THE PREFERRED EMBODIMENTS

Referring to the accompanying drawings, the detailed description will be given hereinafter concerning an embodiment of a method of mass-analyzing a body fluid and an apparatus therefor according to the present invention. Incidentally, the embodiment of the present invention described hereinafter is an example that makes it possible to perform component analysis of in-brain substances while carrying out mass analysis of a cerebral spinal fluid in real time.

Figure 1:
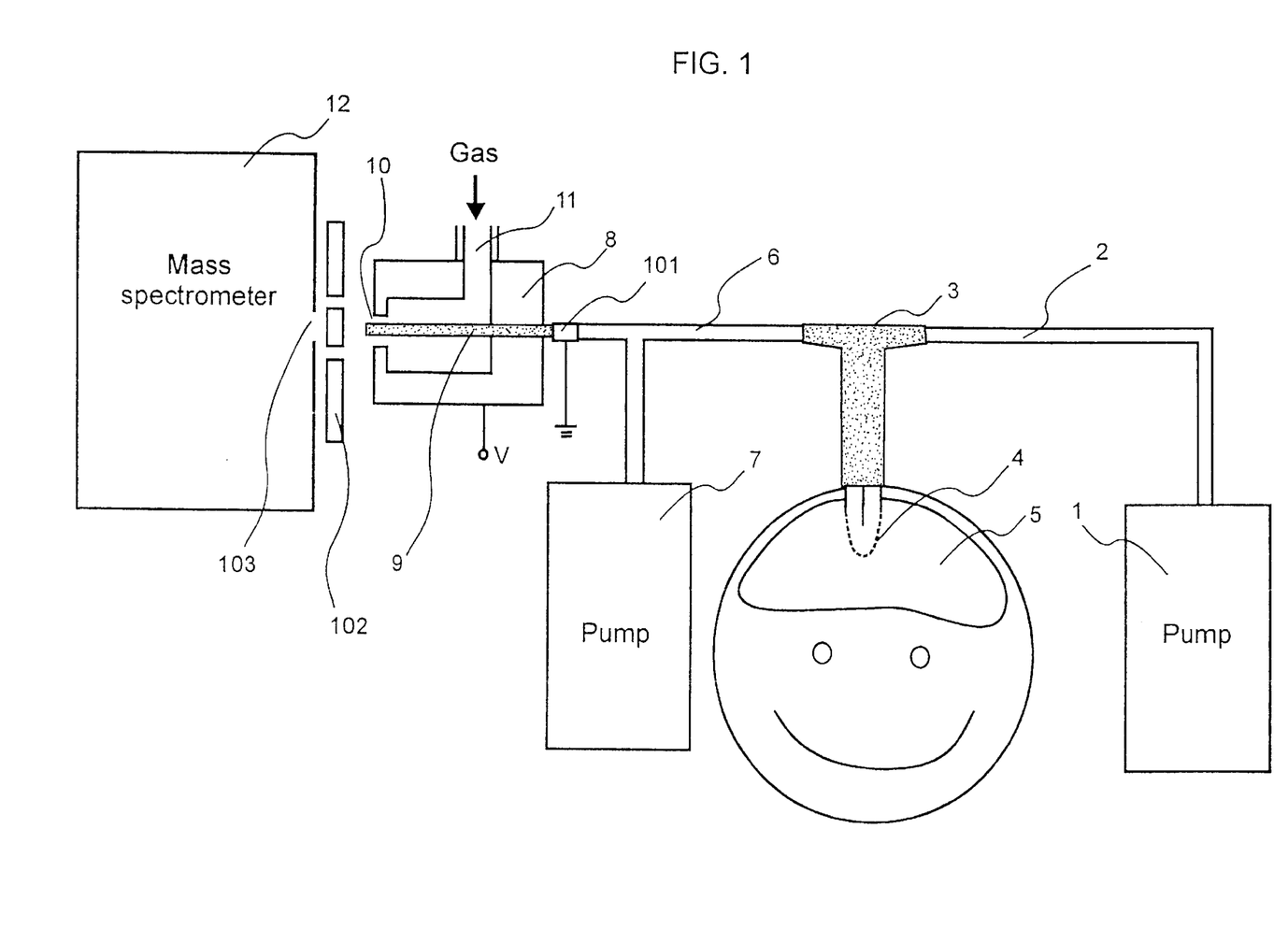
FIG. 1 is a diagram explaining a mass-analyzing method for detecting substances contained in a cerebral spinal fluid by means of a mass-analyzing apparatus according to an embodiment of the present invention.
Figure 2:
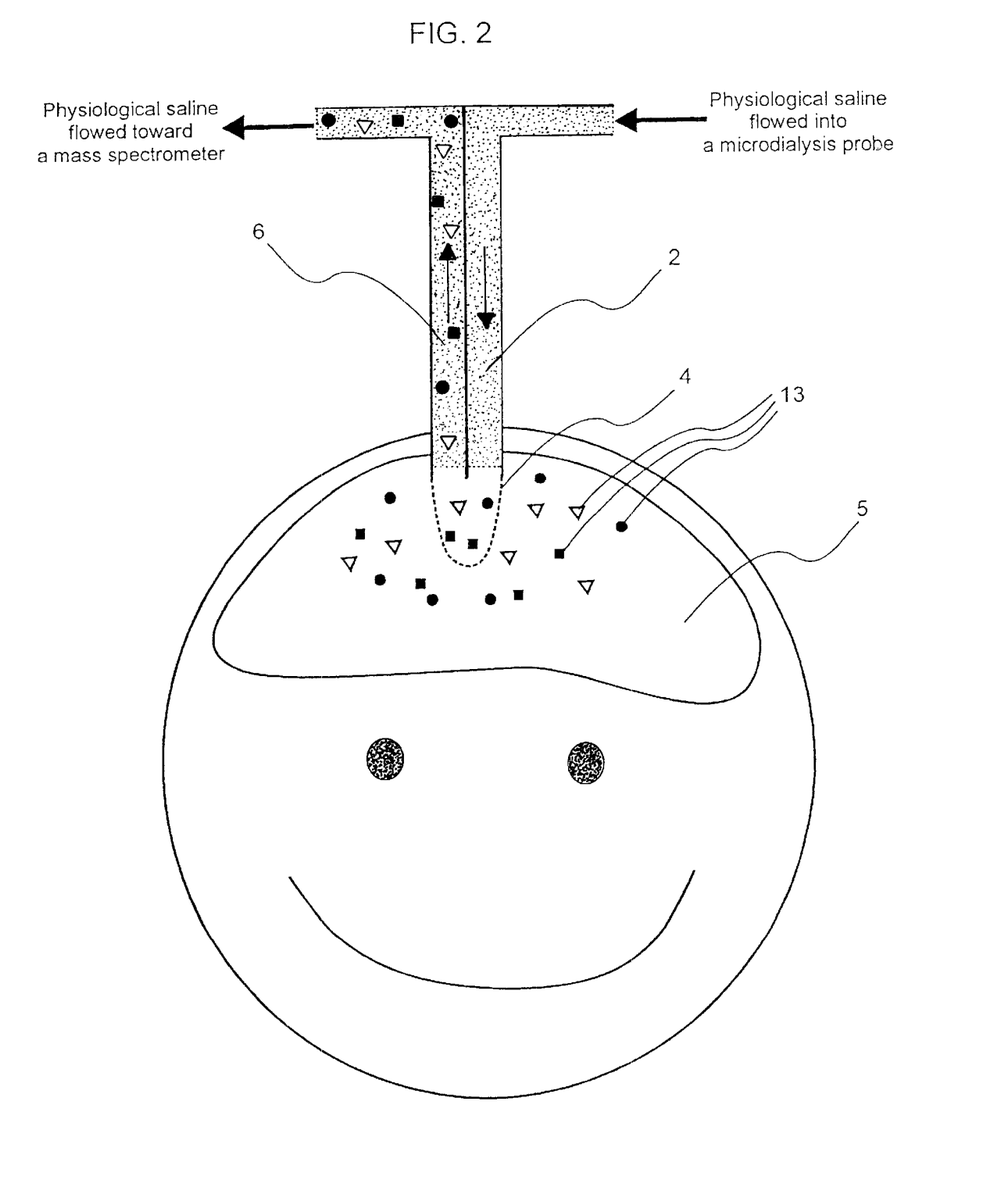
FIG. 2 is a diagram explaining a detailed structure of a microdialysis probe and its operation.
Figure 3:
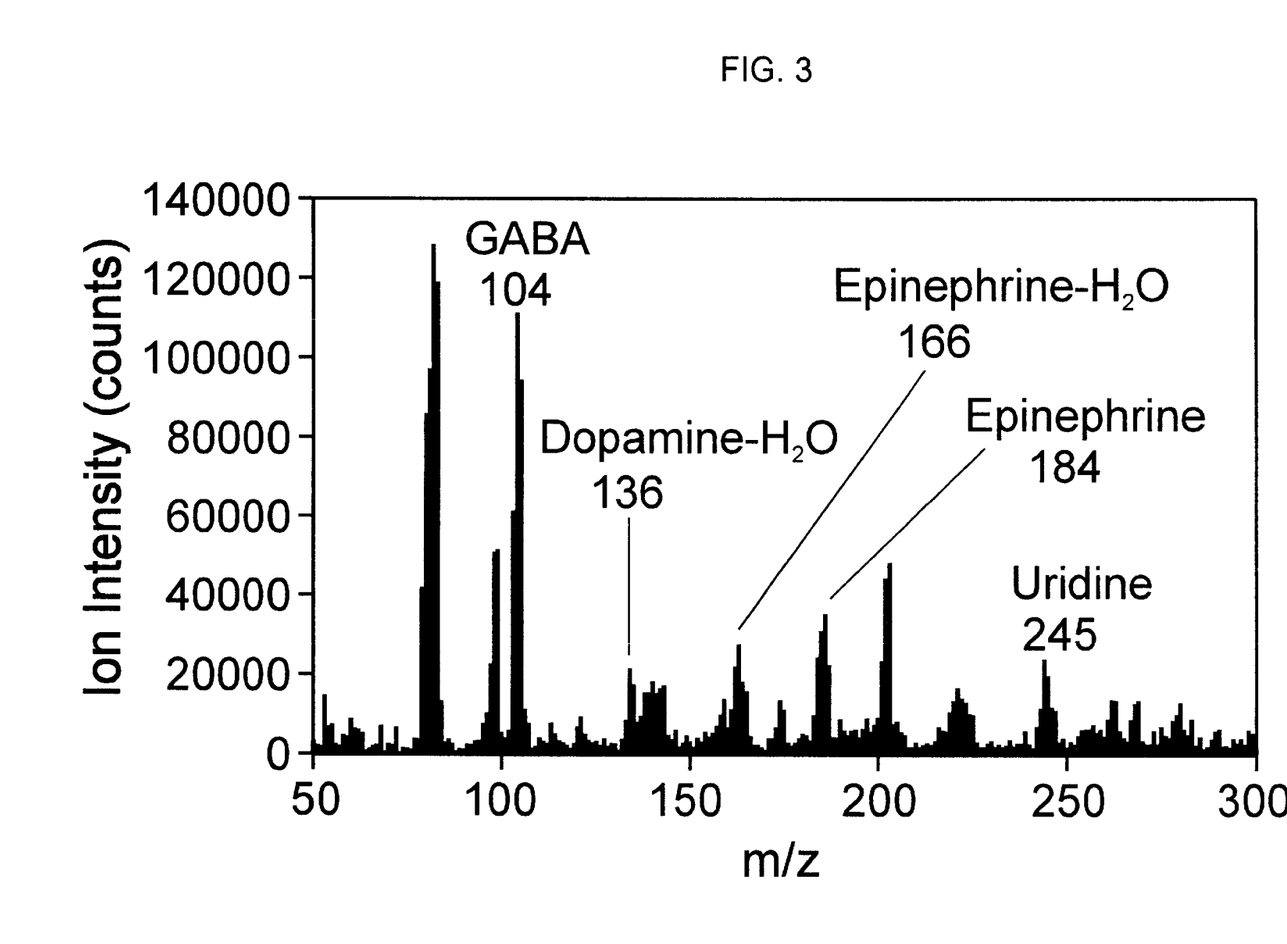
FIG. 3 is a diagram showing a mass spectrum of the cerebral spinal fluid measured by the mass-analyzing apparatus according to the embodiment of the present invention.
Figure 4:
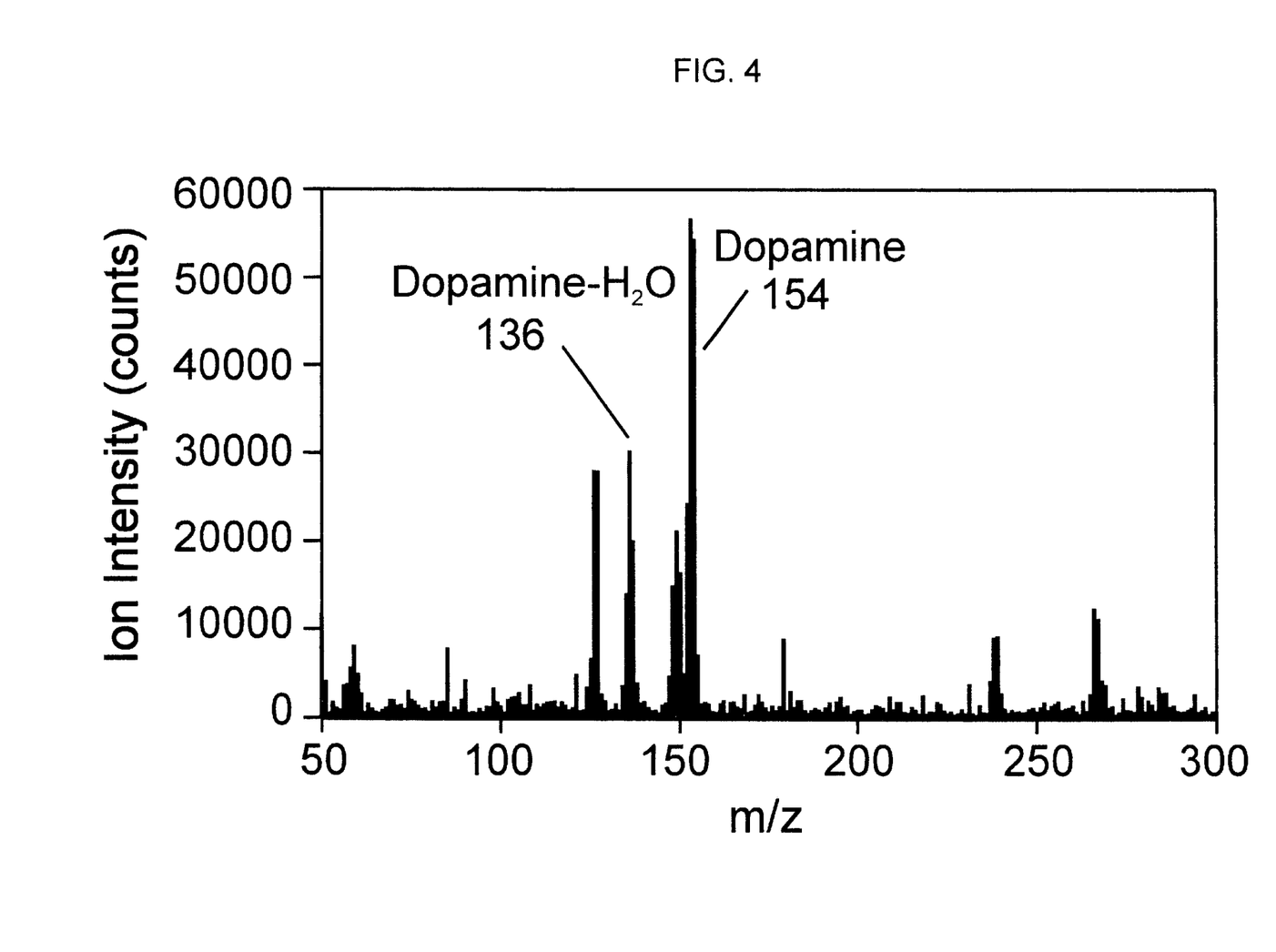
FIG. 4 is a diagram showing a mass spectrum of a dopamine standard measured by the mass-analyzing apparatus according to the embodiment of the present invention.
Figure 5:
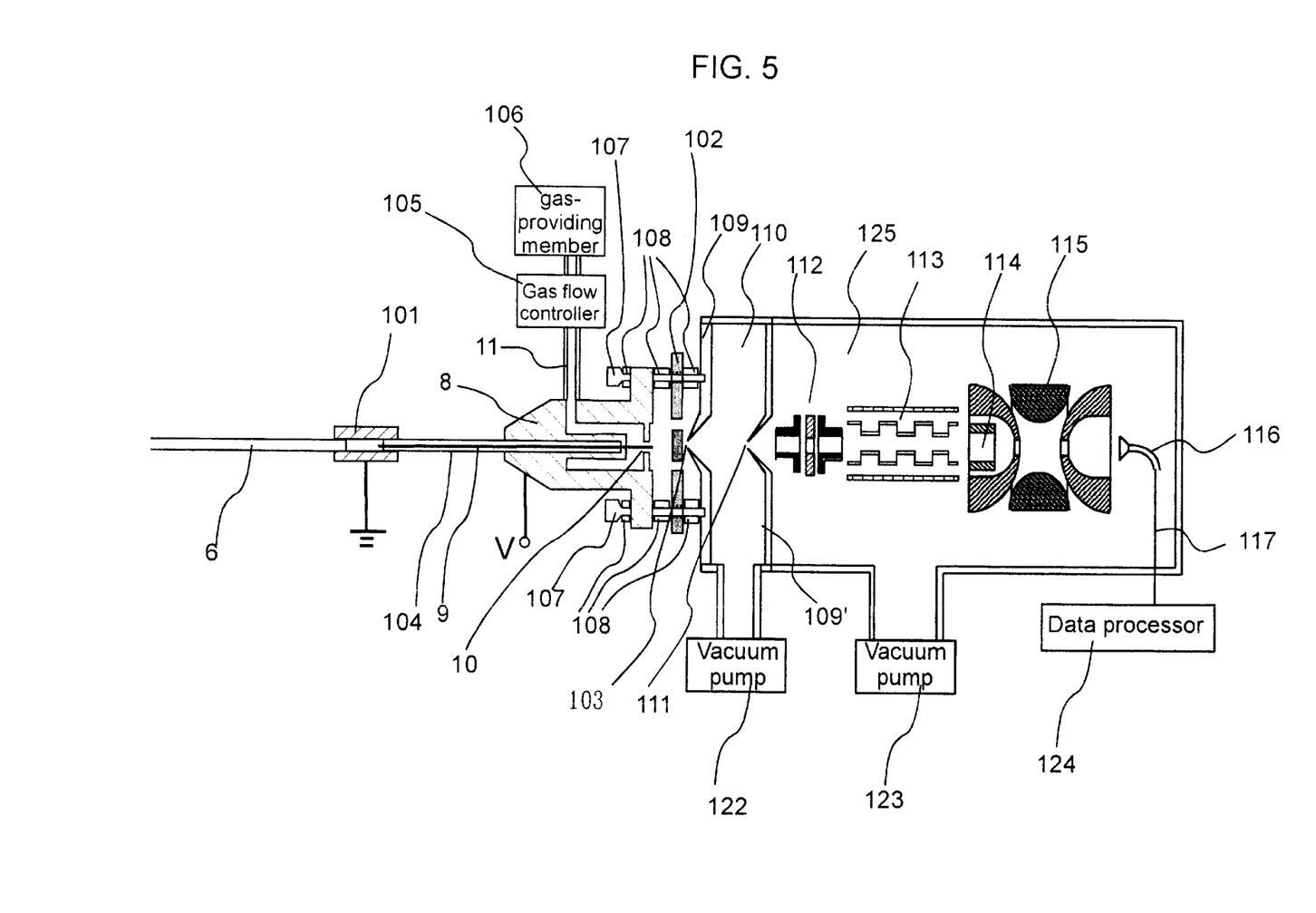
FIG. 5 is a block diagram explaining a configuration of the mass-analyzing apparatus according to the embodiment of the present invention.
Figure 6:
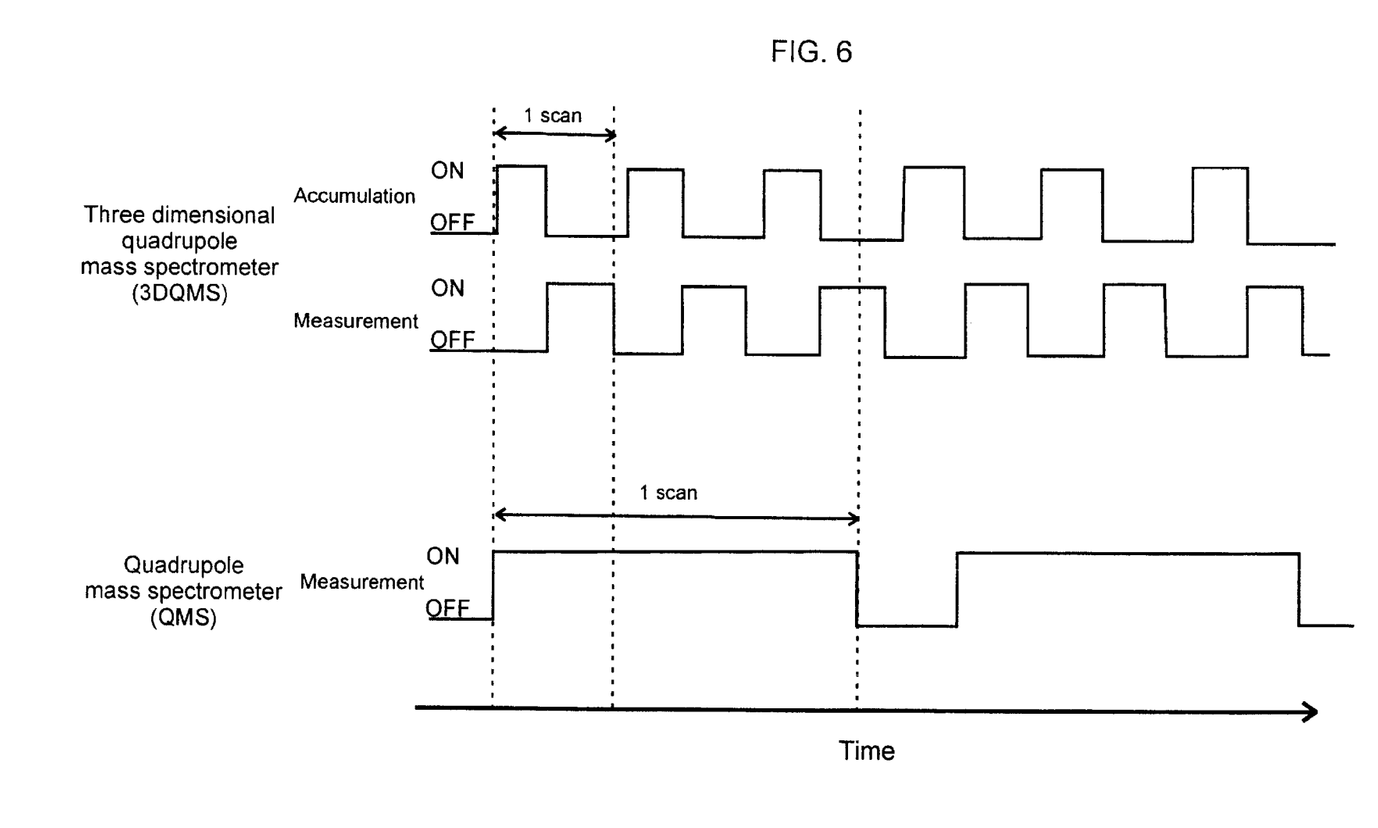
FIG. 6 is a diagram explaining time sequences of measurements performed by a three dimensional quadrupole mass-analyzing apparatus and a quadrupole mass-analyzing apparatus.

FIG. 1 is a diagram explaining a mass-analyzing method for detecting substances contained in a cerebral spinal fluid by means of a mass-analyzing apparatus according to an embodiment of the present invention. FIG. 2 is a diagram explaining a detailed structure of a microdialysis probe and its operation. FIG. 3 is a diagram showing a mass spectrum of the cerebral spinal fluid measured by the mass-analyzing apparatus according to the embodiment of the present invention. FIG. 4 is a diagram showing a mass spectrum of a dopamine standard measured by the mass-analyzing apparatus according to the embodiment of the present invention. FIG. 5 is a block diagram explaining a configuration of the mass-analyzing apparatus according to the embodiment of the present invention. FIG. 6 is a diagram explaining a time sequence of a measurement performed by a three dimensional quadrupole mass-analyzing apparatus and a quadrupole mass-analyzing apparatus. In FIG. 1, FIG. 2 and FIG. 5, the reference numerals denote the components as designated below: 1, 7 pump, 2, 6 flowing passage, 3 microdialysis probe, 4 dialysis membrane, 5 brain, 8 ionization source housing, 9 capillary, 10 orifice, 11 gas-flowing passage 12 mass spectrometer, 13 in-brain substances, 101 metallic tube, 102 plate-like member, 103, 111 orifice, 104 fluoroplastic tube, 105 gas flow controller, 106 gas-providing member, 107 screw, 108 insulator, 109, 109' flange, 110 intermediate pressure region, 112 einzel lens, 113 electrostatic ion-guide, 114 gate electrode, 115 three dimensional quadrupole mass analyzer, 116 detector, 117 cable, 122, 123 vacuum pump, 124 data processor, 125 high vacuum region.

The mass analysis according to the embodiment of the present invention illustrated in FIG. 1 is based on a mass-analyzing method that makes it possible to perform component analysis of in-brain substances in real times while collecting the in-brain substances in the cerebral spinal fluid within the brain 5 of an animal to be inspected. This mass-analyzing method is carried out by an apparatus that includes an sonic spray ionization source and the mass spectrometer 12 having the orifice 103. The sonic spray ionization source includes the pump 1 for sending out a physiological saline, a Ringer or an artificial cerebral spinal fluid into the flowing passage 2, the microdialysis probe 3 connected with the flowing passage 2 and inserted into the brain 5 for sending out the cerebral spinal fluid containing the in-brain substances into the flowing passage 6, the pump 7 for injecting a high volatile organic solvent into the cerebral spinal fluid at a middle point of the flowing passage 6, the ionization source housing 8, the capillary 9, the orifice 10, and the gas-flowing passage 11.

Moreover, the mass spectrometer 12 used in the embodiment of the present invention is an ion trap three dimensional quadrupole mass spectrometer (3DQMS). The plate-like member 102 is located just in front of the orifice 103 of the mass spectrometer 12. Also, the metallic tube 101 connects the flowing passage 6 with the capillary 9. A voltage for promoting ionization of the cerebral spinal fluid as a sample is applied between the metallic tube 101 and the ionization source housing 8. Electric potential of the metallic tube 101 is ground potential as shown in FIG. 5. Also, gas such as nitrogen gas is introduced from the gas-flowing passage 11 of the ionization source housing 8. Here, velocity of the gas flow is adjusted so that, at the orifice 10, it becomes substantially equal to the sonic velocity.

In the above-described embodiment of the present invention, the pump 1 sends out a solution such as the physiological saline, the Ringer or the artificial cerebral spinal fluid, the osmotic pressure of which is close to that of the body fluid, into the flowing passage 2, then sending the solution into the microdialysis probe 3. Here, the physiological saline, which is 0.9% sodium chloride (NaCl)-water solution (w/w), exhibits substantially the same osmotic pressure as that of the body fluid. Also, the Ringer and the artificial cerebral spinal fluid exhibit substantially the same osmotic pressure as that of the physiological saline, and in addition to the sodium chloride, they contain salts of substances such as magnesium or potassium.

The dialysis membrane 4 is provided in the proximity of a tip of the microdialysis probe 3. The microdialysis probe 3 is inserted into the brain 5 so that a portion of the dialysis membrane 4 comes into contact with the brain 5. The in-brain substances existing within the brain 5 pass through the dialysis membrane 4, then entering the solution which is sent into the microdialysis probe 3 by the pump 1 and the osmotic pressure of which is close to that of the body fluid. At this time, substances having a large molecular weight, for example, a protein, cannot pass through the dialysis membrane 4, and accordingly do not enter the solution the osmotic pressure of which is close to that of the body fluid.

The solution, into which the in-brain substances have been dissolved and the osmotic pressure of which is close to that of the body fluid, is introduced into the flowing passage 6. The flowing passage 6 is branched at a middle point thereof. The pump 7, which is provided at the end of a flowing passage branched from the flowing passage 6, introduces a high volatile organic solvent, for example, methanol, into the flowing passage 6. The solution the osmotic pressure of which is close to that of the body fluid is mixed with the methanol, thus being formed as an analyte solution. The methanol assists vaporization of the analyte solution, thus promoting the ionization thereof. At this time, it is allowable that a branched portion is further provided at the above-mentioned branched portion of the flowing passage 6 with a valve provided therebetween, and a minute quantity of acid is introduced from here simultaneously while adjusting the quantity to be mixed. The acid assists ionization of the in-brain substances.

The analyte solution formed by the mixture with the organic solvent is introduced into the fused-silica capillary 9 which is provided in the ionization source housing 8 and the tip of which is inserted in the orifice 10. The gas for causing the analyte solution to be sprayed is introduced into the ionization source housing 8 through the gas-flowing passage 11, and then the gas flows along an outside periphery of the capillary 9. Moreover, when the gas flows out into the atmosphere from the orifice 10 substantially at the sonic velocity, it sprays the analyte solution that flows out of the capillary 9.

At this time, it is allowable that the metallic tube 101 is provided between the flowing passage 6 and the capillary 9 so as to apply the voltage between the metallic tube 101 and the ionization source housing 8. The application of this voltage, after the analyte solution has been sprayed, allows the ionization to be promoted. However, this ionization itself is possible without the application of the voltage.

Ions of the in-brain substances, which are generated in the sprayed gas, are introduced into the mass spectrometer 12 through the orifice 103 of the mass spectrometer 12, thereby performing the mass analysis thereof. By the way, nonvolatile contaminants are contained in the analyte solution sprayed from the capillary 9. The plate-like member 102 is provided at the front of the orifice 103 in order to prevent the nonvolatile contaminants from adhering to the surroundings of the orifice 103. For this purpose, an aperture the central axis of which is shifted from that of the orifice 103 is bored in the plate-like member 102.

Concerning the contaminants contained in the analyte solution sprayed from the capillary 9, if there exist only a small quantity of contaminants, it is allowable not to provide the plate-like member 102.

The above-mentioned embodiment of the present invention makes it possible to, directly and without using any separation tool, send the analyte solution containing the cerebral spinal fluid, i.e. a sample extracted from a living body, into the ionization source and to ionize and mass-analyze it. Consequently, the embodiment makes it possible to carry out the mass analysis in real time and with a high time resolution. Namely, the method presented in the embodiment of the present invention, in which the mass analysis is carried out directly without using any separation tool, is extremely effective in the use for monitoring living body information that is changing from moment to moment.

Additionally, in the case of the conventional techniques that use any separation tool, the sample is collected from the living body with a certain fixed time interval and is injected into a separation tool so as to be separated, and then the separated substances are measured. Accordingly, it was impossible to carry out the mass analysis in real time. Also, a result obtained is an average value within a certain fixed time, and thus the time resolution was found to be no good.

Next, referring to FIG. 2, the description will be given below concerning a detailed structure of the microdialysis probe 3 and its operation.

As illustrated in FIG. 2, the flowing passage 2 and the flowing passage 6 are connected with each other at a tip portion of the microdialysis probe 3. The dialysis membrane 4 is provided in the proximity of this connection portion. The solution the osmotic pressure of which is close to that of the body fluid flows from the flowing passage 2 to the flowing passage 6 through a portion at which the dialysis membrane 4 is provided. The vicinity of the dialysis membrane 4 is inserted into the brain 5. The in-brain substances 13, which exist within the brain 5 and are substances other than the substances having a large molecular weight such as a protein, enter the solution such as the physiological saline through the dialysis membrane 4, then being sent to the mass spectrometer 12 through the flowing passage 6.

The embodiment of the present invention, based on the above-described configuration, makes it possible to perform measurements of cerebral functions in real time. Furthermore, the embodiment allows the dissolved substances to be extracted without collecting the body fluid from the living body, thus making it possible to reduce a burden on the body to be inspected.

A spectrum illustrated in FIG. 3 is a mass spectrum of a cerebral spinal fluid. The spectrum results from an example in the case where an analyte solution is formed by adding 45% of methanol and 5% of acetic acid.

In the illustrated example, peaks corresponding to masses of GABA, epinephrine and uridine, i.e. neurotransmitters within the brain, are observed. Also, when representing a molecular weight of a substance by m and its amount of charge by z, a peak for a substance that remains when a water molecule comes off from dopamine and a peak for a substance that remains when a water molecule comes off from the epinephrine are observed in the vicinities of values of m/z=136, 166, respectively.

It is based on the reason explained below to be able to identify substances for these peaks with the substances that remain when the water molecule comes off from the dopamine or the epinephrine. Namely, employing, as an analyte solution, a dopamine standard solution that is a 1 μmol/liter dopamine concentration of water solution to which 50% of methanol is added, the analyte solution has been measured. The resultant mass spectrum obtained is illustrated in FIG. 4. It can be said that, since the analyte solution is a solution of the pure dopamine, the peaks in the spectrum originate from the dopamine except for the peaks originating from the solvents, i.e. the methanol and the water.

A peak for the dopamine itself can be confirmed at a value of m/z=154, and the other peaks have been confirmed. These other peaks, judging from values of its m/z, can be considered as a peak for a substance that remains when the dopamine is oxidized and thus a hydrogen molecule comes off therefrom and as a peak for a substance that remains when the dopamine is dehydrated and thus a water molecule comes off therefrom. Meanwhile, as seen already in the spectrum illustrated in FIG. 3, in the spectrum in FIG. 3, too, the peak is observed at the same position as that of the dopamine from which the water molecule comes off and which is observed in FIG. 4. Consequently, the peak at the value of m/z=136 in FIG. 3 can be identified as a peak for the substance originating from the dopamine. Although not illustrated, the above-mentioned reason is the same concerning the epinephrine, too.

As described above, even if a substance to be identified has been altered by causes such as the oxidation or the dehydration, the use of the mass-analyzing apparatus according to the embodiment of the present invention makes it possible to recognize an existence of the original substance and, what is more, to recognize relative quantities of a plurality of original substances contained in an analyte solution such as a body fluid. Also, the use of mass-analyzing apparatus makes it possible to judge the degree of the oxidation or the dehydration.

On the other hand, when measuring the dopamine with the use of the electrochemical detection method cited as the conventional technique, it is impossible to perform the measurement thereof except for the measurement of the dopamine that has not decomposed at all (m/z=154). Accordingly, if a time has elapsed since collection of the sample and the hydrogen molecule or the water molecule has come off, the value to be measured varies and thus it becomes impossible to perform the identification.

Next, referring to FIG. 5, the description will be given below concerning a concrete configuration of the mass-analyzing apparatus according to the embodiment of the present invention. This embodiment is configured by combining the sonic spray ionization source with the 3DQMS.

The sonic spray ionization source, as was described referring to FIG. 1, includes the ionization source housing 8, the capillary 9, the orifice 10, and the gas-flowing passage 11. FIG. 5 shows that the sonic spray ionization source further includes the gas flow controller 105 provided at a middle point of the gas-flowing passage 11 and the gas-providing member 106. Moreover, the screw 107 fixes the sonic spray ionization source and the plate-like member 102, which is illustrated in FIG. 1 as well, to the first flange 109 in which the orifice 103 of the 3DQMS 12 is provided. The insulator 108, which is located among the ionization source housing 8, the plate-like member 102 and the first flange 109, insulates the three components to each other.

The 3DQMS 12 includes the intermediate pressure region 110, which is evacuated by the vacuum pump 122 and formed between the first flange 109 and the second flange 109' having the second orifice 111, and the high vacuum region 125 which is evacuated by the second vacuum pump 123 and in which members such as the mass analyzer are located. Furthermore, the einzel lens 112, the electrostatic ion-guide 113, the gate electrode 114, the three dimensional quadrupole mass analyzer 115 and the detector 116 are provided within the high vacuum region 125. An output of the detector 116, through the cable 117, is sent to the data processor 124 such as a personal computer and is processed, thereby being displayed as a graph or the like representing the spectral distribution or being printed out.

In the embodiment of the present invention configured described above, the analyte solution containing the in-brain substances is introduced into the ionization source housing 8 through the flowing passage 6 and the metallic tube 101. Between the ionization source housing 8 formed of a metal and the metallic tube 101, it is allowed to apply a high voltage of about −1.2 kV on the side of the ionization source housing 8. This is intended to generate an electric field between the ionization source housing 8 and the metallic tube 101 so that the analyte solution is positioned in the electric field, as a result, positive ions can be extracted more effectively. Incidentally, it is not necessarily required to ground the metallic tube 101. It is sufficient to apply the voltage so that the electric field is applied to the sample solution.

A voltage of +150V is applied to the first flange 109. Also, a configuration of the first flange 109 may be a configuration in which a portion of the orifice 103 is projected on the side of the plate-like member 102, or may be a plane-like configuration. Although the insulator 108 insulates the ionization source housing 8, the plate-like member 102 and the first flange 109 to each other, it is allowable to apply a different voltage to them each. Also, it is allowable to locate a heater on the plate-like member 102 and heat it.

The sample solution, which have passed through the metallic tube 101, is introduced into the capillary 9 extending through the fluoroplastic tube 104. The tip portion of the capillary 9 is inserted in the orifice 10. Gas such as nitrogen gas or the air is introduced from the gas-providing member 106 into the ionization source housing 8 through the gas flow controller 105 and the gas-flowing passage 11. Flow quantity of the gas is adjusted by the gas flow controller 105 provided at the middle point of the gas-flowing passage 11. Then, the gas flows out into the atmosphere from the orifice 10 substantially at the sonic velocity and sprays the sample solution that flows out of the capillary 9, thereby ionizing under the atmospheric pressure the in-brain substances contained in the sample solution.

The generated ions pass through the aperture in the plate-like member 102 and the orifice 103, and are introduced into the intermediate pressure region 110 evacuated by the vacuum pump 122, then being introduced through the second orifice 111 into the high vacuum region 125 evacuated by the vacuum pump 123. A voltage of about +160V, which is about 10V higher than the voltage applied to the first flange 109, is applied to the second flange 109' in which the second orifice 111 is provided. The ions having passed through the second orifice 111 pass through the einzel lens 112, the electrostatic ion-guide 113 and the gate electrode 114, then being introduced into the three dimensional quadrupole mass analyzer 115.

The gate electrode 114, using a voltage applied thereto, permits incidence of the ions into an ion trap portion from the outside while accumulating the ions, and, while measuring the ions, permits emission of the ions from the ion trap portion to the outside, thus introducing the ions into the three dimensional quadrupole mass analyzer 115. The ions introduced into the three dimensional quadrupole mass analyzer 115 are exhausted while being mass-separated in a direction opposite to the direction in which the ions had been introduced. Then, the exhausted ions collide with the detector 116, thereby being detected. At this time, it is allowable to configure the embodiment by equating the ion-introduced direction with the ion-exhausted direction. The output signal of the detector 116 is sent through the cable 117 to the data processor 124 such as a personal computer and is processed, thereby being displayed as a graph or the like representing the spectral distribution or being printed out.

In the embodiment of the present invention, as described above, by employing the mass spectrometer that includes the three dimensional quadrupole mass analyzer having the ion trap portion, it is possible to perform the mass analysis concerning a small quantity of sample solution in a short while and with a high sensitivity.

Next, referring to FIG. 6, the description will be given below concerning time sequences of analyses performed by the three dimensional quadrupole mass spectrometer (3DQMS) employed in the present invention and a quadrupole mass spectrometer (QMS) in the conventional techniques.

The 3DQMS is an ion trap mass spectrometer, in which a single measurement (1 scan) of a mass spectrum consists of a process of accumulating the ions (accumulation) and a process of performing the measurement. In this measurement, range width of the mass spectrum can be set freely within a specified range. Accumulation time can also be set freely within a specified range. As the accumulation time is set to be longer, quantity of accumulated ions can be increased and intensity of measured ions can be heightened. Also, measurement time changes, depending on the set range width of the mass spectrum.

The 3DQMS stores ions the masses of which are within a specified range within the set accumulation time. Next, the 3DQMS expels the stored ions from an ion accumulation unit in the order of increasing or decreasing masses, then sending them into the detector and performing the mass measurement. A time for the one scan thereof is short, falling in the range of a few milliseconds to a few hundred milliseconds.

Meanwhile, the QMS in the conventional techniques, which does not necessitate the process of storing the ions, can perform the single measurement (1 scan) only with the process of the measurement. The QMS permits only an ion having a specific mass to pass through and sends it into the detector, thereby separating the ion. Moreover, the QMS changes, in the order of increasing or decreasing masses, masses of the ions that can pass through the QMS, thereby obtaining the mass spectrum. Range width of the mass spectrum in the QMS can be set freely within a specified range. Also, a time for the one scan depends on the set range width of the mass spectrum, falling in the range of a few hundred milliseconds to a few seconds. Also, the QMS does not store the ions, and accordingly the ion quantity in the one scan (signal quantity) is smaller as compared with the case of the 3DQMS. This condition forces the QMS to performs the measurement for a longer time interval as compared with the case of the 3DQMS, thus making it necessary to integrate the mass spectrum over so many scans.

As described above, the QMS in the conventional techniques requires the measurement for a longer time interval, and what is more, necessitates an even larger quantity of the sample in comparison with the case of using the 3DQMS. However, the living body fluid such as the cerebral spinal fluid, i.e. an object of the measurement performed by the embodiment of the present invention, cannot be collected in large amounts, and thus there exists a limit to the quantity of the sample. This situation makes it difficult to perform the measurement with the use of the QMS.

In contrast with this situation, the embodiment of the present inventions makes it possible to perform the mass analysis in a short while, using a minute quantity of sample. Generally speaking, functions of the brain are embodied by mutual operations among a plurality of substances. Accordingly, in order to realize the cerebral functions, it is necessary to know ratio of concentrations among respective substances secreted within the brain. By the way, as illustrated in FIG. 3, the above-mentioned embodiment of the present invention makes it possible to recognize the ratio of concentrations among the in-brain substances in real time. Consequently, the embodiment of the present invention makes it possible to perform analysis of the in-brain substances in response to a change of the living body.

The above-described detailed description concerning the embodiment of the present invention has been given in such a manner that the embodiment is able to measure the in-brain substances in the cerebral spinal fluid in real time. The present invention, however, is able to identify in real time various kinds of substances that are contained in living body fluids other than the cerebral spinal fluid, such as a spinal fluid, and that vary with a lapse of time. Also, the present invention makes it possible not only to perform the real time measurement but also to perform measurement of collected samples using a batch processing.

As described above, even toward the body fluid, i.e. an analyte solution in which the substances contained vary with a lapse of time and which has an extremely high electrical conductivity, the present invention allows the ionization thereof to be performed in a short while, thus making it possible to mass-analyze the analyte solution in a short while. As a result, it becomes possible to mass-analyze living body substances, in particular, neurotransmitters in a state in which they really are in the living body, although it was impossible for the conventional techniques to perform such type of mass analysis.

What is claimed is:

1. A mass-analyzing method comprising the steps of:

using a microdialysis probe for collecting living body fluid from a living body;

applying analyte solution including the living body fluid collected by the microdialysis probe to a first flowing passage;

mixing the analyte solution with an organic solvent introduced from a passage branched from said first flowing passage;

flowing a gas around a second flowing passage connected with said first flowing passage through which the analyte solution mixed with the organic solution flows;

spraying and ionizing the analyte solution from said second flowing passage by the gas so as to provide ionized ions; and mass-analyzing the ionized ions in real time.

2. A mass-analyzing method according to claim 1, further comprising a step of introducing a solution into a primary side of said microdialysis probe.

3. A mass-analyzing method according to claim 1, wherein said living body fluid is a cerebral spinal fluid or a spinal fluid.

4. A living body fluid mass-analyzing method comprising the steps of:

introducing a first solution whose osmotic pressure is close to that of a living body fluid into a microdialysis;

extracting the living body fluid from said microdialysis;

mixing the living body fluid from said microdialysis and an organic solution;

applying a gas around a capillary through which the mixed living fluid flows thereby spraying and ionizing the living body fluid by the gas so as to provide ionized ions;

introducing the ionized ions into a three dimensional mass-analyzer through an orifice;

accumulating the ions in said three dimensional mass-analyzer; and sending out the accumulated ions in order of mass to measure mass numbers of the ions.

5. A living body fluid mass-analyzing method according to claim 4, further comprising a step of repeating a plurality of scans to output a result thereof, each of the scans being said accumulating step and said sending-out step.

6. A living body fluid mass-analyzing method according to claim 5, wherein a period of time for one scan falls in a range of a few milliseconds to a few hundred milliseconds.

* * * * *